(12) United States Patent
Zider et al.

(10) Patent No.: US 9,474,541 B2
(45) Date of Patent: Oct. 25, 2016

(54) SURGICAL DEVICES

(71) Applicants: John R Zider, Portola Valley, CA (US); Robert B Zider, Portola Valley, CA (US)

(72) Inventors: John R Zider, Portola Valley, CA (US); Robert B Zider, Portola Valley, CA (US)

(*) Notice: Subject to any disclaimer, the term of this patent is extended or adjusted under 35 U.S.C. 154(b) by 244 days.

(21) Appl. No.: 13/798,125

(22) Filed: Mar. 13, 2013

(65) Prior Publication Data

US 2014/0276831 A1    Sep. 18, 2014

(51) Int. Cl.
*A61B 17/16* (2006.01)
*A61B 17/32* (2006.01)
*A61B 17/00* (2006.01)

(52) U.S. Cl.
CPC ..... *A61B 17/32002* (2013.01); *A61B 17/1637* (2013.01); *A61B 17/1642* (2013.01); *A61B 2017/00309* (2013.01); *A61B 2017/00862* (2013.01); *A61B 2017/00867* (2013.01); *A61B 2017/00946* (2013.01)

(58) Field of Classification Search
USPC .......................................... 606/79, 80, 82–85
See application file for complete search history.

(56) References Cited

U.S. PATENT DOCUMENTS

| | | | |
|---|---|---|---|
| 4,020,847 A * | 5/1977 | Clark, III | 606/159 |
| 4,646,738 A | 3/1987 | Trott | |
| 5,035,696 A * | 7/1991 | Rydell | 606/47 |
| 5,250,059 A | 10/1993 | Andreas | |
| 5,254,130 A | 10/1993 | Poncet | |
| 5,411,514 A | 5/1995 | Fucci | |
| 5,488,761 A * | 2/1996 | Leone | 29/2.25 |
| 5,620,447 A * | 4/1997 | Smith et al. | 606/79 |
| 5,669,926 A | 9/1997 | Aust | |
| 5,833,692 A | 11/1998 | Cesarini | |
| 5,921,956 A * | 7/1999 | Grinberg et al. | 604/95.01 |
| 6,290,709 B1 | 9/2001 | Ellis | |
| 6,337,142 B2 * | 1/2002 | Harder et al. | 428/573 |
| 6,740,030 B2 | 5/2004 | Martone | |
| 7,585,300 B2 * | 9/2009 | Cha | 606/80 |
| 7,951,161 B2 | 5/2011 | Bonnette | |
| 2008/0125799 A1 | 5/2008 | Adams | |
| 2010/0087711 A1 | 4/2010 | Edwards | |
| 2010/0211076 A1 * | 8/2010 | Germain et al. | 606/84 |
| 2011/0071356 A1 | 3/2011 | Edwards | |

* cited by examiner

*Primary Examiner* — Nicholas Woodall
(74) *Attorney, Agent, or Firm* — T. H. P. Richardson (57) ABSTRACT

An endoscopic surgical instrument for removing tissue or bone, the instrument comprising (1) a generally tubular component (2) a cutting device which is housed in the distal end member and part of which protrudes beyond the window in the distal member, and (3) a means for operating the cutting device. The tubular component comprises a distal end member containing a cutting device, a proximal member, and between the distal member and the proximal member a hollow, generally tubular intermediate member which deforms elastically when the angle between the distal member family proximal member is changed. The intermediate member can for example be composed of a nickel titanium alloy, and/or can be slotted, and/or can be in the form of an accordion, and/or be in the form of a coil.

18 Claims, 5 Drawing Sheets

SURGICAL DEVICES

FIELD OF THE INVENTION

This invention relates to endoscopic surgical instruments.

BACKGROUND OF THE INVENTION

Endoscopic surgical instruments for removing tissue or bone are known. Such instruments generally comprise a hollow tubular proximal member, a hollow distal end member having a window therein, a cutting device which is housed in the distal end member and part of which protrudes beyond the window in the distal member, and a shaft which passes through the proximal member and operates the cutting device. The term "cutting device" is used in this specification to include any device which can be used to cut or debride bone or tissue, including but not limited to blades, burs and microdebriders. The term "endoscopic" is used in this specification to include, but is not limited to, procedures such as arthroscopy, laparoscopy, subdermal percutaneous surgery, ENT, trauma, subacromial decompression, acromioplasty, notchplasty for ligament repair, osteochondral debridement for osteochondral defect, ACL, OCD repair in the knee, and other minimally invasive surgical procedures. For information about known endoscopic surgical instruments, reference may be made, for example to U.S. Pat. Nos. 4,646,738, 5,250,059, 5,254,130, 5,411,514, 5,669,926, 5,833,692, 6,290,709, and 7,951,161, US Patent Publications 2008/0125759, 2011/0071356 and 2010/0087711 The entire disclosure of each of those patents and publications is incorporated herein by reference for all purposes.

SUMMARY OF THE INVENTION

It has been discovered, in accordance with the present invention, that improved results can be obtained with endoscopic surgical instruments containing a cutting device by placing an elastically deformable member close to the distal member containing the cutting device and between the distal member and the proximal member. The elastically deformable member makes it easier for the operator to maintain the shaver blade in a desired position relative to the material to be removed. The operator can change the relative position of the cutting device and the material to be removed by pressing the distal member against the surface itself or against an adjacent surface. In this way, if the operator wishes, less or more of the cutting device can be brought into contact with the material to be removed.

In a first aspect, this invention provides a generally tubular component which is particularly, but not exclusively, useful as a component of an endoscopic surgical instrument for removing tissue or bone, the component comprising (1) a hollow, generally tubular distal end member which
   (a) has a first distal axis, (b) is rigid, and (c) comprises a window which exposes a substantial part of the interior of the distal end member, and
(2) a proximal member which (a) is rigid, and (b) comprises a first proximal section which is adjacent to the distal end member and which has a first proximal axis which is usually the same as the first distal axis but can be different from the first distal axis, and
(3) between the distal end member and the proximal member, a hollow, generally tubular intermediate member which deforms elastically when the angle between the first distal axis and the first proximal axis is changed.

As further described below, the proximal member can be straight, or it can comprise the first straight proximal section and a second straight proximal section which is remote from the distal end member and which is at an angle to the first proximal section. The axis of the intermediate member is generally, but not necessarily, the same as the first distal axis. The axis of the intermediate member is generally, but not necessarily, the same as the first proximal axis.

Each of the members (1), (2) and (3) preferably ha a substantially circular cross-section, with the cross-section of the proximal member being the same as or slightly greater than the cross-section of the intermediate member, and the cross-section of the intermediate member being the same as or slightly greater than the cross-section of the distal member, and the invention will be described chiefly with reference to such members. However, the invention includes the possibility that the members have a different hollow cross-section, for example an oval cross-section. Because the distal end member comprises a window which exposes a substantial part of the interior of the distal end member, the part of the distal end member which defines the window has a cross-section which is only part of a circular cross-section.

In a second aspect, this invention provides an endoscopic surgical instrument for removing tissue or bone, the instrument comprising (1) a generally tubular component according to the first aspect of the invention, (2) a cutting device which is housed in the distal end member and part of which protrudes beyond the window in the distal member, and (3) a means for operating the cutting device, for example a shaft which attached to the cutting device and which extends through the intermediate member and the proximal member. The operator of such an endoscopic surgical instrument can control the angle at which the cutting device bears upon the surface of the material to be removed by forcing the distal end member against the surface itself or against an adjacent surface, thus deforming the intermediate member. The surgical instruments of the second aspect of the invention can, but preferably do not, comprise additional means for controlling the angle between the distal and proximal members.

In a third aspect, this invention provides a method of removing tissue and/or bone which comprises applying the cutting device of a surgical instrument according to the second aspect of the invention to the tissue or bone

BRIEF DESCRIPTION OF THE DRAWINGS

The invention is illustrated in the accompanying drawings, in which.

DETAILED DESCRIPTION OF THE INVENTION

Figure 1A:
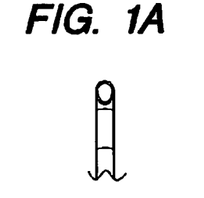
FIGS. 1A, 1B and 1C illustrate part of three exemplary components of the first aspect of the invention in which the intermediate member is a collar which is composed of a nickel-titanium ("Nitinol") alloy, and the proximal member is straight and is aligned with the distal member (FIG. 1A, "straight"), or the proximal member is bent so that the window is aligned with the proximal member (FIG. 1B, "pre-curved extension"), or the proximal member is bent so that the window is not aligned with the proximal member (FIG. 1C, "pre-curved flexion")
Figure 1B:
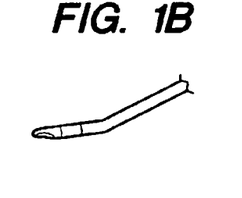
Figure 1C:
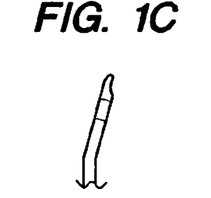
Figure 2A:
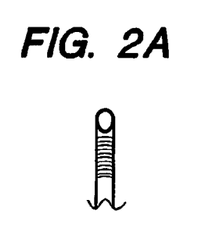
FIGS. 2A, 2B and 2C illustrate part of three exemplary components of the first aspect of the invention in which the intermediate member is a slotted collar, and the proximal member is straight and is aligned with the distal member (FIG. 2A, "straight"), or the proximal member is bent so that the window is aligned with the proximal member (FIG. 2B, "pre-curved extension"), or the proximal member is bent so that the window is not aligned with the proximal member (FIG. 2C, "pre-curved flexion")
Figure 2B:
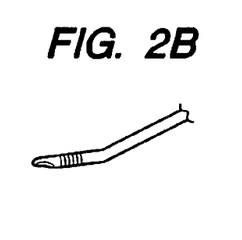
Figure 2C:
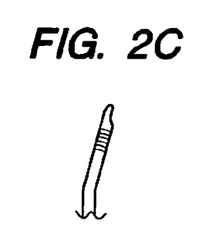
Figure 3A:
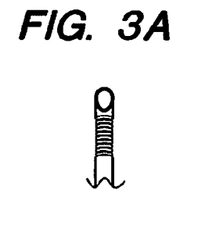
FIGS. 3A, 3B and 3C illustrates part of three exemplary components of the first aspect of the invention in which the intermediate member is an accordion collar, and the proximal member is straight and is aligned with the distal member (FIG. 3A, "straight"), or the proximal member is bent so that the window is aligned with the proximal member (FIG. 3B, "pre-curved extension"), or the proximal member is bent so that the window is not aligned with the proximal member (FIG. 3C, "pre-curved flexion")
Figure 3B:
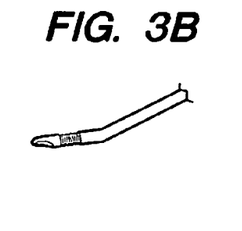
Figure 3C:
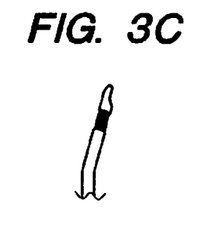
Figure 4A:
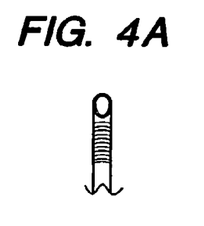
FIGS. 4A, 4B and 4C illustrate part of three exemplary components of the first aspect of the invention in which the intermediate member is a coiled collar, and the proximal member is straight and is aligned with the distal member (FIG. 4A, "straight"), or the proximal member is bent so that the window is aligned with the proximal member (FIG. 4B, "pre-curved extension"), or the proximal member is bent so that the window is not aligned with the proximal member (FIG. 4C, "pre-curved flexion")
Figure 4B:
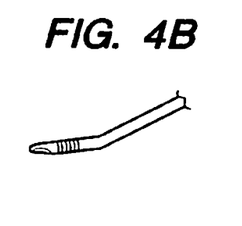
Figure 4C:
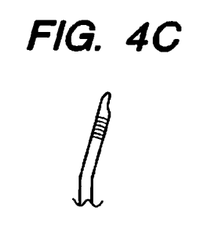
Figure 5:
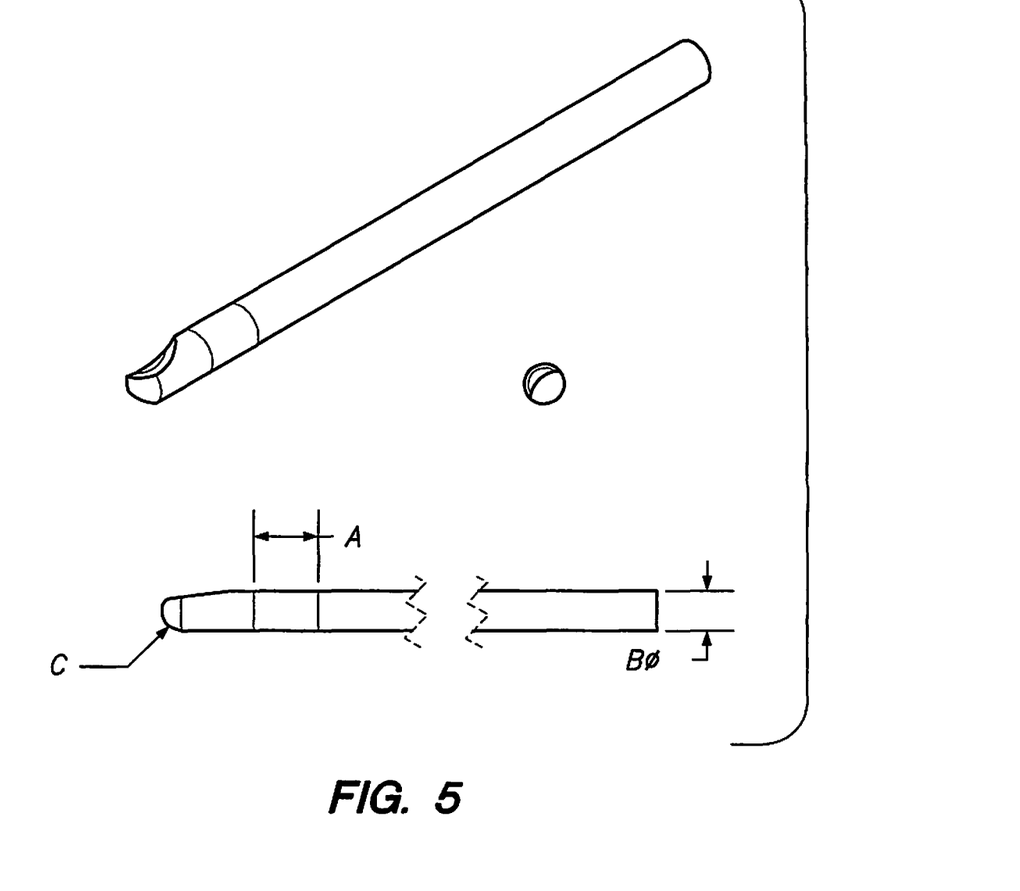
FIG. 5 shows perspective, side and end views of the component shown in FIG. 1A.
Figure 6:
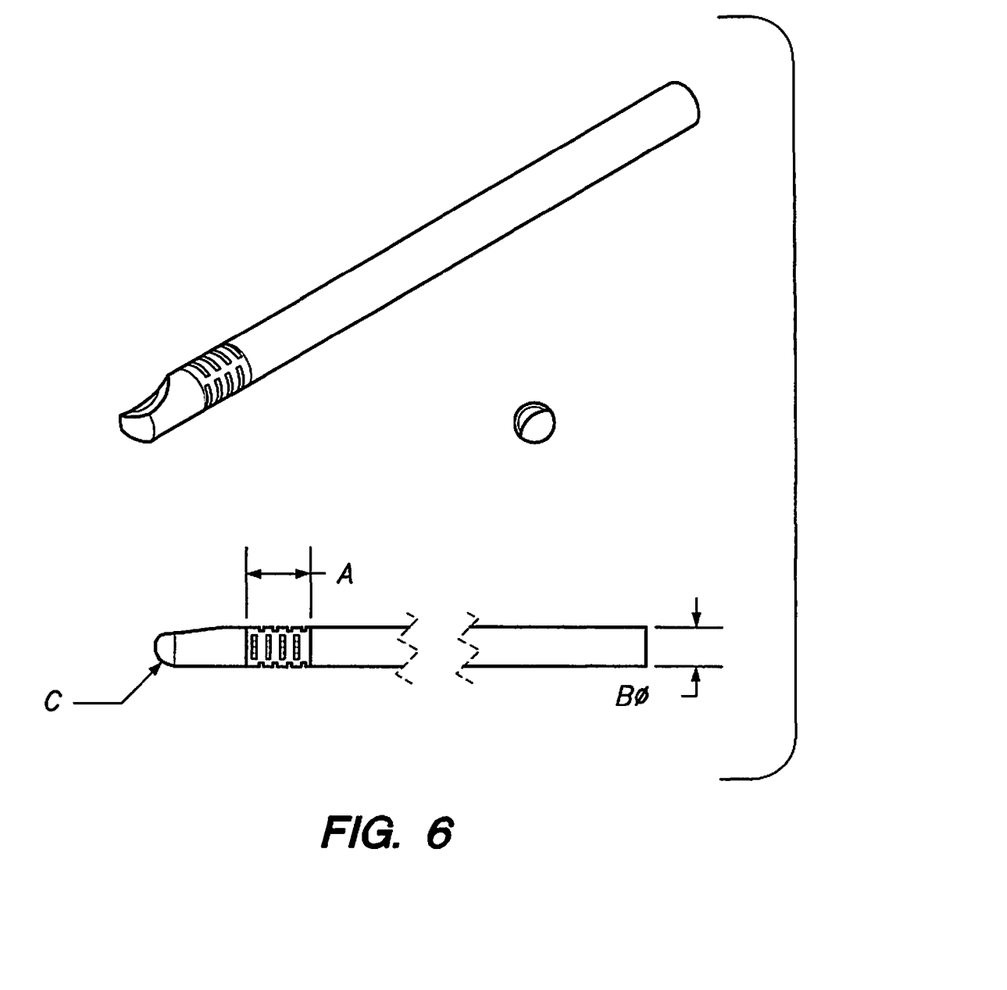
FIG. 6 shows perspective, side and end views of the component shown in FIG. 2A.
Figure 7:
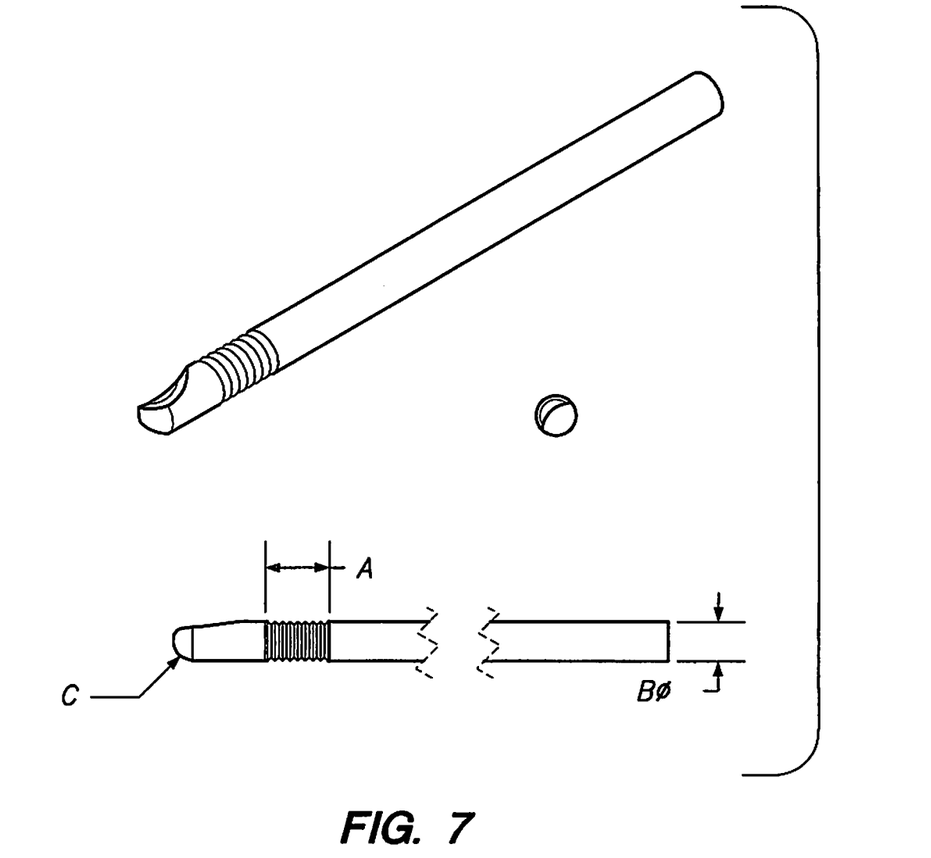
FIG. 7 shows perspective, side and end views of the component shown in FIG. 3A.
Figure 8:
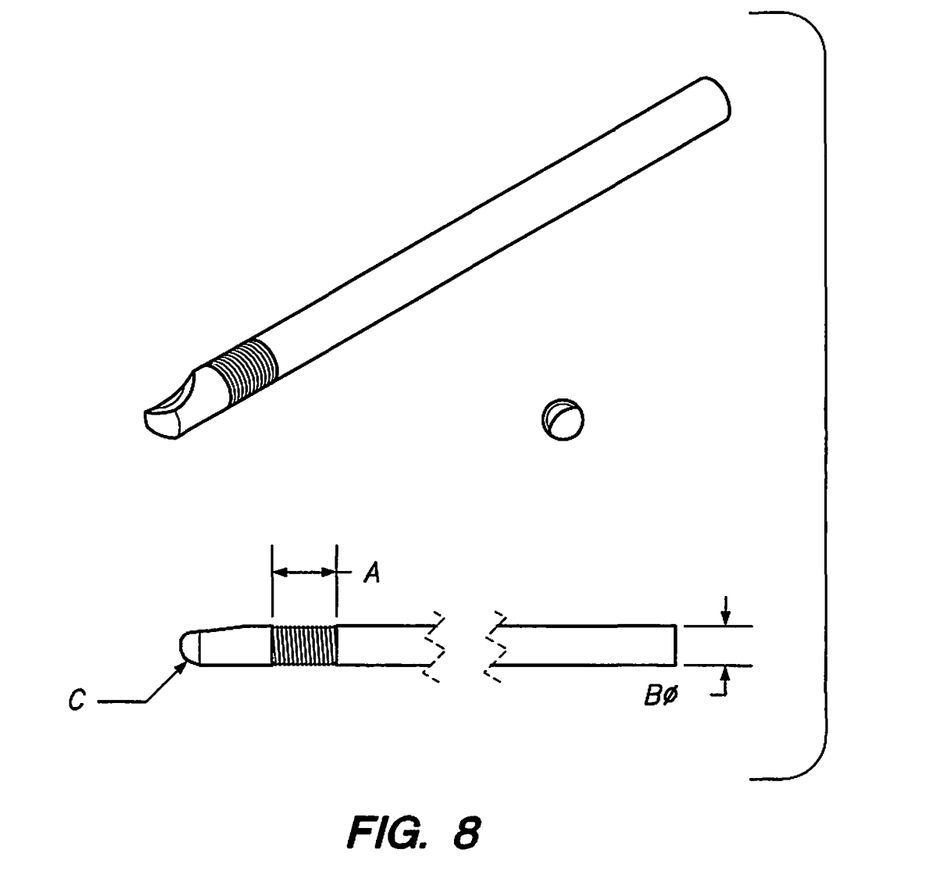
FIG. 8 shows perspective, side and end views of the component shown in FIG. 4A.

In the Summary of the Invention above, the Detailed Description of the Invention below, and the accompanying drawings, reference is made to particular features (including for example components, ingredients, elements, devices, apparatus, systems, groups, ranges, method steps, test results, etc.) of the invention. It is to be understood that the disclosure of the invention in this specification includes all possible combinations of such particular features. For example, where a particular feature is disclosed in the context of a particular aspect, a particular embodiment, a particular claim, or a particular Figure, that feature can also be used, to the extent appropriate, in the context of other particular aspects, embodiments, claims and Figures, and in the invention generally. The invention disclosed includes embodiments not specifically described herein and can for example make use of features which are not specifically described herein, but which provide functions which are the same, equivalent or similar to, features specifically disclosed herein.

The term "comprises" and grammatical equivalents thereof are used herein to mean that, in addition to the features specifically identified, other features are optionally present. For example, a composition or device "comprising" (or "which comprises") components A, B and C can contain only components A, B and C, or can contain not only components A, B and C but also one or more other components. The term "consisting essentially of" and grammatical equivalents thereof is used herein to mean that, in addition to the features specifically identified, other features may be present which do not materially alter the claimed invention. The term "at least" followed by a number is used herein to denote the start of a range beginning with that number (which may be a range having an upper limit or no upper limit, depending on the variable being defined). For example "at least 1" means 1 or more than 1, and "at least 80%" means 80% or more than 80%. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When a range is given as "(a first number) to (a second number)" or "(a first number)-(a second number)", this means a range whose lower limit is the first number and whose upper limit is the second number. For example, "from 8 to 20 carbon atoms" or "8-20 carbon atoms" means a range whose lower limit is 8 carbon atoms, and whose upper limit is 20 carbon atoms. The terms "plural", "multiple", "plurality" and "multiplicity" are used herein to denote two or more than two features.

Where reference is made herein to a method comprising two or more defined steps, the defined steps can be carried out in any order or simultaneously (except where the context excludes that possibility), and the method can optionally include one or more other steps which are carried out before any of the defined steps, between two of the defined steps, or after all the defined steps (except where the context excludes that possibility). Where reference is made herein to "first" and "second" features, this is generally done for identification purposes; unless the context requires otherwise, the first and second features can be the same or different, and reference to a first feature does not mean that a second feature is necessarily present (though it may be present). Where reference is made herein to "a" or "an" feature, this includes the possibility that there are two or more such features (except where the context excludes that possibility). Where reference is made herein to two or more features, this includes the possibility that the two or more features are replaced by a lesser number or greater number of features providing the same function (except where the context excludes that possibility). The numbers given herein should be construed with the latitude appropriate to their context and expression; for example, each number is subject to variation which depends on the accuracy with which it can be measured by methods conventionally used by those skilled in the art. The term monolithic is used herein to denote an article which has substantially the same composition throughout.

This specification incorporates by reference all documents referred to herein and all documents filed concurrently with this specification or filed previously in connection with this application, including but not limited to such documents which are open to public inspection with this specification.

The terms nickel-titanium and nickel-titanium alloy (also referred to herein as Nitinol) are used in this specification to denote an alloy which consists essentially of nickel and titanium, or which alternatively consists essentially of nickel and titanium and a small quantity, e.g. less than 5%, of one or more other metals. The proportion of titanium can for example be 40-80% by weight. In some embodiments, the alloy contains 48-55% of titanium. For further information about nickel titanium alloys, reference may be made to U.S. Pat. Nos. 5,398,916; 5,842,312; 6,796,408; 7,398,964; US 2009/002-5833; WO 2007/039271; Duerig et al, Engineering Aspects of Shape Memory Alloys, 1990; and Krumme et al. Proceedings of SPIE, San Diego, Calif., USA, v. 2445, pp 225-240. The entire disclosure of each of those patents and literature references is incorporated herein by reference for all purposes. Some embodiments of the present invention make use of a super elastic nickel titanium alloy, and those skilled in the art will have no difficulty, having regard to their own knowledge and the disclosure in this specification (including the documents incorporated by reference herein), in identifying suitable intermediate components comprising super elastic nickel titanium alloys for use in this invention The different aspects of the invention can optionally have the features set out above, and the features enumerated below. The features set out above and enumerated below can be present in any combination of two or more of those features, except when the features are mutually exclusive.

The Intermediate Member.

The intermediate member can optionally have one or more of the following features.

(1) The intermediate member comprises a nickel titanium alloy, preferably a superelastic nickel titanium alloy. The intermediate member can for example be (a) a simple cylinder of a nickel titanium alloy, (b) a cylinder of a nickel titanium alloy having a transverse pleats therein, for example pleats which extend around the circumference of the cylinder to form an accordion, (c) a cylinder of a nickel titanium alloy having slots variant, or (d) a coil of a nickel titanium alloy wire. When the intermediate member is a cylinder of a nickel titanium alloy having slots therein, the slots can for example be transverse slots which are at right angles to the axis of the cylinder and which extend around 15-90% of the circumference of the cylinder and which are staggered, so that the elastic deformation of the intermediate member does not depend upon the direction of the force exercised upon it. In another embodiment, the slots are at an angle to the axis of the cylinder and are arranged in an asymmetric pattern so that the elastic deformation of the intermediate member depends upon the direction of the force exercised upon it. When the intermediate member has slots therein, it preferably also comprises an elastically deformable polymeric sleeve which covers the slots. A deformable polymeric sleeve can also be present to cover an intermediate member which has transverse pleats therein or which is a coil.

An advantage of using an intermediate member which comprises a nickel titanium alloy is that the member and the alloy from which it is made can be chosen to produce a desired resistance to bending up to a desired maximum which cannot be exceeded, but from which the intermediate member will recover to its original shape when the pressure is released.

(2) The intermediate member is in the form of an accordion and is composed of a resilient material, for example an elastomeric polymer.

(3) The intermediate member is in the form of a coil and is composed of a resilient material, for example a metal, for example stainless steel or titanium.

(4) The intermediate member comprises a plurality of spaced-part transverse slots which are separated by solid members which are elastically deformed when the angle between the first and second axes is changed. Such an intermediate member may be composed of a metal, for example stainless steel or titanium (5) The intermediate member can be elastically deformed to an extent which accommodates a change of the angle between the first distal axis and the first proximal axis of at least 5°, preferably at least 10°, for example in the range 10 to 50°, preferably 10 to 30°.

(6) The window has a periphery which extends to the end of the distal member.

(7) The distance between (1) the edge of the window which is closest to the intermediate member and (2) the part of the intermediate member which is closest to the window, is 0.5 to 3 mm, for example 1 to 2 mm.

(8) The length of the intermediate member is 3 to 12 mm, for example 4.5 to 9.5 mm The Proximal Member.

The proximal member can be straight, or it can comprise a first straight section which is adjacent to the intermediate member and which has a first proximal axis, and a second straight section which is remote from the intermediate member and which has a second proximal axis which is at an angle, for example an angle of 3 to 30°, to the first proximal axis.

The Spatial Relationship Between the Window and the Proximal Member.

When the proximal member is straight, the first and second proximal axes are the same, and pass through the window in the distal member. When the proximal member comprises a first straight section adjacent to the intermediate member and a second straight section at an angle thereto, the window preferably opens in a plane which is at right angles to a plane containing the first and second proximal axes.

The Drawings.

In the drawings, the length of the collar is designated A and can be for example 5, 6, 7, 8 or 9 mm; the outer diameter of the proximal member is designated B and can be for example 2.39, 3.50, 4.15, 5.00 and 5.48 mm respectively; and the outer diameter of the distal member is for example 2.28, 3.23, 3.83, 4.73 and 5.14 mm respectively.

Further Description of the Invention Follows.

A preferred use of the present invention is the optimization of cutting/resection during endoscopic procedures. The elastically deformable intermediate section permits increased surface area contact during the resection and/or debridement of soft tissue, cartilage, ligament and/or bone during endoscopic procedures; particularly arthroscopy. Optimal surface contact is achieved due to the intermediate member located just millimeters below the cutting window; thus, when applying pressure to the patient's bone and/or tissue, improved surface contact is achieved. Current designs offer insufficient contact on irregular surface areas. Many also kink or clog and are limited in respect to cannula sizes. When applying pressure to the desired cutting surface, the flexible distal end located just below the cutting window can be repeatedly flexed throughout any procedure without deformation to the elongated outer sheath and inner-cutting-shaft. The flexible section of the stainless steel/titanium sheath can be made from any biocompatible materials, including but not limited to a shape memory alloy known as Nitinol, titanium, stainless steel, polymer, etc. The flexible section can be designed in a number of ways to allow flexibility once the surgeon applies minimal pressure onto the desired cutting surface. Nitinol has shape memory properties that can be specifically tailored to flex up to a maximum deformation and return to the original once pressure is released. The maximum deformation of a member composed of a nickel titanium alloy can be correlated to the amount of pressure applied. The minimum amount of pressure to allow flexibility applied can also be tailored. Thus, the maximum flexibility and minimal pressure applied are controllable. The flexible section of the shaft is located millimeters below the cutting window, and can be ¼ to ½ inches in length. This flexible Nitinol section can be ribbed like an accordion or be flush with the titanium/stainless steel sheath. The tip can be predesigned as straight shaft, curved and/or in an upward or downward angle, thus, maximizing surface contact depending the surgical application (e.g. resurfacing the condyle, subacromial decompression, etc.) Other methods for allowing the tip to flex up to a predetermined max point and return to the original orientation (pre-angled or straight) without deformation can be used with other biocompatible materials such as stainless steel, titanium, and polymers. The flexing section could be designed with a specific number of slits oriented in a fashion to allow flexibility of the material, a coil-style encapsulated with a biocompatible coating, ribbed similar to an accordion, etc.

The flexible section is located millimeters underneath the cutting window, being minimal in size. As mentioned above, an example during subacromial decompression in the shoulder, a straight-edged shaft only makes full surface-to-window contact with bone on a flat surface. This is also true during knee arthroplasty with the curvature anatomy of the condyle. The present invention mitigates these issues with a pre-curved, controlled flexing portion located millimeters beneath the cutting window. Thus, a downward or pre-curved sheath when resecting a flat surface would be straight when full pressure is applied, and mimic the anatomy when less pressure is a applied to irregular or curved surfaces. The inner cutting shaft and outer sheath will flex in accordance to the patient's anatomy. These sheath would be able to flex in a straight position during cannula insertion; thus users are not limited to certain cannula sizes.

A principal purpose of this invention is to provide an efficient cutting window, thus optimizing full surface contact between the cutting window and the patient's bone, tissue etc. This will benefit both patients and surgeons.

The invention claimed is:

1. An endoscopic surgical instrument for removing tissue or bone, the instrument comprising
    (A) a generally tubular component which comprises
        (1) a hollow, generally tubular distal end member which (a) has a first distal axis, (b) is rigid, and (c) comprises a window which exposes a substantial part of the interior of the distal end member,
        (2) a hollow, generally tubular proximal member which (a) is rigid, and (b) comprises a first proximal section which is adjacent to the distal end member and which has a first proximal axis, and
        (3) between the distal end member and the proximal member, a hollow, generally tubular intermediate member which
            (i) connects the distal end member and the proximal member,
            (ii) has a first configuration having an axis
            (ii) deforms elastically from the first configuration to a second configuration when the distal end member is pressed against a surface, thus changing the angle between the first distal axis and the first proximal axis, and
            (iii) returns to the first configuration when the distal end member is no longer pressed against a surface;
    (B) a cutting device which is housed in the distal end member and part of which protrudes beyond the window in the distal member, and
    (C) a shaft which is attached to the cutting device and which extends through the intermediate member and the proximal member.

2. A method of removing tissue or bone which comprises applying the cutting device of a surgical instrument as defined in claim 1 to the tissue or bone, and operating the cutting device.

3. An instrument according to claim 1 wherein the first proximal axis, the first distal axis and the axis of the intermediate member are the same.

4. An instrument according to claim 1 wherein the first proximal axis is different from the first distal axis.

5. An instrument according to claim 1 in which the intermediate member is the sole means for controlling the angle between the first proximal axis and the first distal axis.

6. An instrument according to claim 1 wherein the length of the intermediate member is 3 to 12 mm.

7. An instrument according to claim 1 wherein the length of the intermediate member is 4.5 to 9.5 mm.

8. An instrument according to claim 1 wherein the distance between (1) the edge of the window which is closest to the intermediate member and (2) the part of the intermediate member which is closest to the window is 0.5 to 3 mm.

9. An instrument according to claim 1 wherein the distance between (1) the edge of the window which is closest to the intermediate member and (2) the part of the intermediate member which is closest to the window is 1 to 2 mm.

10. An instrument according to claim 1 wherein the intermediate member can be elastically deformed to an extent which accommodates a change of the angle between the first distal axis and the first proximal axis of at least 5°.

11. An instrument according to claim 1 wherein the intermediate member is in the form of a coil composed of a resilient metal.

12. An instrument according to claim 11 wherein the coil is composed of a metal selected from stainless steel or titanium.

13. An instrument according to claim 1 wherein the intermediate member comprises a superelastic nickel titanium alloy.

14. An instrument according to claim 1 wherein the intermediate member comprises a nickel titanium alloy and the intermediate member can be deformed elastically by pressure from an original shape up to a maximum deformation which cannot be exceeded, but from which the intermediate member will recover to its original shape when the pressure is released.

15. An instrument according to claim 1 wherein each of the distal end member, proximal member and intermediate member has a substantially circular cross-section, except that the part of the distal end member which defines the window has a cross-section which is only part of a circular cross-section.

16. An instrument according to claim 1 wherein the cross-section of the proximal member is the same as the cross-section of the intermediate member and the cross-section of the intermediate member is the same as the cross-section of the distal member.

17. An endoscopic surgical instrument for removing tissue or bone, the instrument comprising
    (A) a generally tubular component which comprises
        (1) a hollow, generally tubular distal end member which (a) has a first distal axis, (b) is rigid, and (c) comprises a window which exposes a substantial part of the interior of the distal end member, and
        (2) a hollow, generally tubular proximal member which (a) is rigid, and (b) comprises a first proximal section which is adjacent to the distal end member and which has a first proximal axis which is the same as the first distal axis, and
        (3) between the distal end member and the proximal member, a hollow, generally tubular intermediate member which
            (i) connects the distal end member and the proximal member,
            (ii) has a first configuration,
            (iii) has a length of 3 to 12 mm,
            (iv) has an axis which is the same as the axis of the proximal member and the distal member, (v) deforms elastically from the first configuration to a second configuration when the distal end member is pressed against a surface, thus changing the angle between the first distal axis and the first proximal axis, the extent to which the angle between the first distal axis and the first proximal axis can be changed being at least 5°; and (vi) returns to the first configuration when the distal end member is no longer pressed against a surface;

(B) a cutting device which is housed in the distal end member and part of which protrudes beyond the window in the distal member, and (C) a shaft which is attached to the cutting device and which extends through the intermediate member and the proximal member.

18. A method of removing tissue or bone which comprises applying the cutting device of a surgical instrument as defined in claim 17 to the tissue or bone,-pressing the distal end member against a surface to change the angle between the first distal axis and the first proximal axis, and operating the cutting device.

* * * * *